United States Patent [19]

Sicken

[11] Patent Number: 5,608,100
[45] Date of Patent: Mar. 4, 1997

[54] OLIGOMERIC PHOSPHORIC ACID ESTERS WHICH CARRY HYDROXYALKOXY GROUPS, THEIR PREPARATION AND THEIR USE

[75] Inventor: Martin Sicken, Cologne, Germany

[73] Assignee: Hoechst Aktiengesellschaft, Frankfurt am Main, Germany

[21] Appl. No.: 571,749

[22] Filed: Dec. 13, 1995

Related U.S. Application Data

[63] Continuation-in-part of Ser. No. 354,662, Dec. 13, 1994, abandoned.

[30] Foreign Application Priority Data

Dec. 16, 1993 [DE] Germany .................... 43 42 972.6

[51] Int. Cl.$^6$ ........................................ C07F 9/09
[52] U.S. Cl. .................... 558/164; 558/105; 558/165
[58] Field of Search .................... 558/164, 165, 558/105

[56] References Cited

U.S. PATENT DOCUMENTS

| | | | |
|---|---|---|---|
| 3,764,640 | 10/1973 | Klose | 558/105 |
| 3,767,732 | 10/1973 | Klose | 558/165 X |
| 3,998,764 | 12/1976 | Vollmer et al. | 558/165 X |
| 4,382,042 | 5/1983 | Hardy et al. | 558/164 X |
| 4,697,030 | 9/1987 | Hardy et al. | 558/164 X |

*Primary Examiner*—Johann Richter
*Assistant Examiner*—Michael G. Ambrose
*Attorney, Agent, or Firm*—Connolly and Hutz

[57] ABSTRACT

The invention relates to mixtures of oligomeric phosphoric acid esters which carry hydroxyalkoxy groups, of the formula I

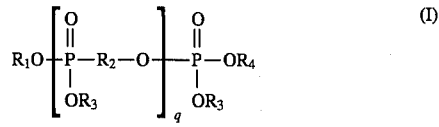

in which
$R_1$ is a hydroxyl-containing radical of the formula IIa,
$R_2$ is a radical of the formula III

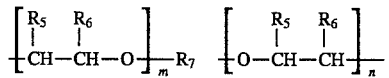

(IIa: $R_7$ = H)  (III)
(IIb: $R_7$ = $C_1$–$C_6$)

$R_3$ is a radical of the formula IIb, $R_4$ is $R_1$ or $R_3$; $R_5$, $R_6$ and $R_7$ are an H atom or an alkyl radical having 1 to 6 carbon atoms, m is 0 to 4, n is 1 to 4 q is 0 to 20 and $\bar{q}$ (the mean) is 0.5 to 10.

The invention also relates to a process for the preparation of the mixtures and to their use as reactive flameproofing agents in polyurethane foams.

5 Claims, No Drawings

OLIGOMERIC PHOSPHORIC ACID ESTERS WHICH CARRY HYDROXYALKOXY GROUPS, THEIR PREPARATION AND THEIR USE

This application is a continuation-in-part of application Ser. No. 08/354,662 field Dec. 13, 1994, now abandoned.

The invention relates to mixtures of oligomeric phosphoric acid esters which carry hydroxyalkoxy groups, and to their preparation and their use as reactive flameproofing agents in polyurethane foams.

Polyurethane foam can be used in fields of use which impose high requirements on the burning properties of the materials employed (for example automobile interior fittings and building insulations) only with the aid of the additional use of flameproofing agents. The majority of these flameproofing agents, such as, for example, tris (2-chloroethyl) phosphate, tris (chloroisopropyl) phosphate, tris (2,3-dichloropropyl) phosphate and tetrakis (2-chloroethyl) ethylene diphosphate, are incorporated as additives, which can lead to partial emigration thereof under exposure to heat. This adverse effect, which plays a considerable role above all in the case of open-cell foams, not only causes a decrease in the flameproofing action in the course of time and therefore an increase in the content of flameproofing agent to be employed, but also leads to contamination of the environment of the product. Such additive additions thus contribute, for example, to the so-called "fogging", the condensation of vaporized volatile constituents from the motor vehicle interior fittings on the windshield. This phenomenon can be recorded quantitatively in accordance with DIN 75 201.

The use of reactive (instead of additive) flameproofing agents is a considerable improvement in this respect; in the case of polyurethane, for example, the use of phosphorus- and chlorine-containing polyols, which are reacted with polyisocyanates by themselves or as a mixture with conventional polyols and are thus bonded covalently into the polymer matrix.

Products having a good flameproofing action are described in DE-C 20 36 595. These are mixtures of oligomeric phosphoric acid esters, for example of the formula (1)

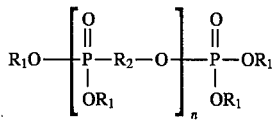

in which n is 0 to 4, $R_1$ is a halogenated alkyl or aryl radical and at least one hydroxyl-containing radical of the formula (2), and $R_2$ is a radical of the formula (3), in which, in the formulae (2) and (3), $R_3$ and $R_4$ are a hydrogen atom or an optionally chlorine-substituted alkyl radical, and m is a number from 1 to 4.

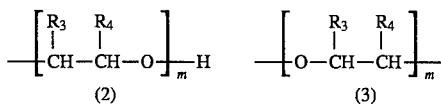

The products of the formula (1) are prepared by reaction of a compound of the formula (4), in which $R_5$ is a halogenated alkyl or aryl radical, with polyphosphoric acid or a mixture of polyphosphoric acid and phosphorus pentoxide and subsequent reaction with an epoxide of the formula (5)

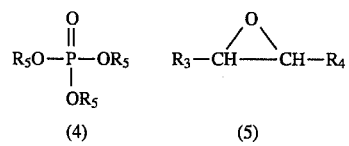

By the process of DE-C 20 36 595 for the preparation of the products of the formula (1), in the particular first process stage, mixtures of polyphosphoric acid partial esters having a varying degree of condensation and inhomogeneous distribution of acid and ester groups among the individual molecules are obtained, which results in about 5 to 25% by weight of neutral phosphoric acid esters being formed. However, since only the acid esters give products which contain hydroxyl-containing radicals of the formula (2) described above in the particular subsequent second process stage with epoxides, the end products of the formula (1) unavoidably also comprise hydroxyl-free components. The mixtures obtained according to DE-C 20 36 595 are thus mixtures of reactive and "additive" products, which have the disadvantages described above, in respect of their reaction with, for example, isocyanates, although according to DE-C 20 36 595, only the content in the mixture of hydroxyl-containing (and thus reactive) esters of the formula (1) is claimed.

DE-C 20 36 587 furthermore describes a process for obtaining reaction products of the formula (1) by reaction of phosphorus pentoxide and/or polyphosphoric acid with halogenated alkanols and phenols and with an epoxide of the formula (5). Although the process of DE-C 20 36 587 ensures preparation exclusively of hydroxyl-containing products, only mixtures of products which contain on average the same number or more hydroxy-alkoxy groups relative to halogen-containing radicals can be obtained in the manner described therein, since in the alcoholysis of P—O—P groupings which takes place in the first process step, in each case an ester and an acid function (P-O-H function) are produced simultaneously, the latter reacting to form a hydroxyl-containing radical in the second process step. Because of the resulting high content of hydroxyl groups [at least 50 mol% of the radicals $R_1$ in formula (1)], however, such mixtures are of only limited suitability as flameproofing agents for flexible polyurethane foams.

The mixtures described in DE-C 20 36 595 and DE-C 20 36 587 furthermore have the common feature, beyond the disadvantages mentioned, that they contain halogens in bonded form as the essential constituent for achieving the flameproofing effectiveness required. This is a disadvantage, since, in the event of a fire, halogen-containing products can liberate corrosive hydrogen halides and under certain circumstances toxic decomposition products.

U.S. Pat. No. 43 82 042 describes the preparation of oligomeric phosphoric acid esters of the formula (6) in which n is 0 to 10, R is an alkyl or haloalkyl radical (C1–C10) and $R_1$ and $R_2$ are hydrogen atoms or alkyl or haloalkyl radicals (C1–C10).

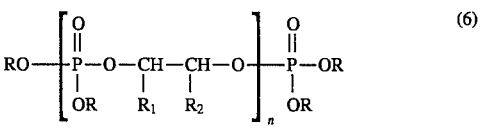

The products of the formula (6) are prepared by successive reaction of phosphorus pentoxide with an orthophosphoric acid ester of the formula (7), in which R has the meaning described above, and with an epoxide of the formula (8), in which $R_1$ and $R_2$ have the meaning given above. Products prepared by this process thus contain no hydroxyl-containing radicals and accordingly can be employed only as additive flameproofing agents.

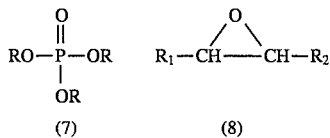

Selective hydrolysis of P—O—P groupings in polyphosphoric acid esters with water is known (Houben-Weyl, Methoden der Organischen Chemie [Methods of Organic Chemistry], 4th Edition, Volume XII/2, page 942).

The object of the present invention was thus to develop novel products which are reactive (i.e. capable of being incorporated) and halogen-free and at the same time have a high permanent flameproofing efficiency when used in polyurethane foam.

This object is achieved by the discovery of mixtures of oligomeric phosphoric acid esters, which carry hydroxyalkoxy groups, of the formula I

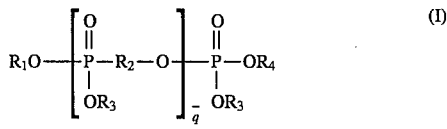

in which $R_1$ is a hydroxyl-containing radical of the formula IIa, $R_2$ is a radical of the formula III

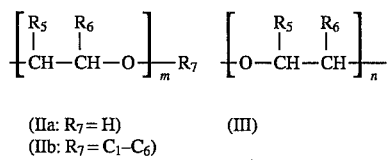

(IIa: $R_7 = H$)
(IIb: $R_7 = C_1-C_6$)

$R_3$ is a radical of the formula IIb, $R_4$ is $R_1$ or $R_3$; $R_5$, $R_6$ and $R_7$ are an H atom or an alkyl radical having 1 to 6 carbon atoms, m is 0 to 4, n is 1 to 4, q is 0 to 20 and $\bar{q}$ (the mean) is 0.5 to 10.

Preferably the mixture of the oligomeric phosphoric acid esters contains 0 to 35% by weight of compounds according to formula I with q=0

0 to 50% by weight of compounds according to formula I with q=1

0 to 30% by weight of compounds according to formula I with q=2

0 to 50% by weight of compounds according to formula I with q=3

0 to 50% by weight of compounds according to formula I with q=4

0 to 30% by weight of compounds according to formula I with q=5

0 to 25% by weight of compounds according to formula I with q=6

0 to 15% by weight of compounds according to formula I with q=7

0 to 15% by weight of compounds according to formula I with q=8 and in which the sum amounts to 100% by weight.

Also it is possible that the mixture of the olibomeric phosphoric acid esters contains 2 to 15% by weight of compounds according to formula I with q=0

5 to 20% by weight of compounds according to formula I with q=1

8 to 30% by weight of compounds according to formula I with q=2

30 to 50% by weight of compounds according to formula I with q=3

8 to 30% by weight of compounds according to formula I with q=4

5 to 30% by weight of compounds according to formula I with q=5

2 to 15% by weight of compounds according to formula I with q=6 and in which the sum amounts to 100% by weight.

Furthermore it is possible that the mixture of the olibomeric phosphoric acid esters contains 15 to 35% by weight of compounds according to formula I with q=0

30 to 50% by weight of compounds according to formula I with q=1

10 to 30% by weight of compounds according to formula I with q=2

5 to 20% by weight of compounds according to formula I with q=3

2 to 10% by weight of compounds according to formula I with q=4 and in which the sum amounts to 100% by weight.

The invention furthermore relates to a possible process for the preparation of the abovementioned novel mixtures of oligomeric phosphoric acid esters which carry hydroxyalkoxy groups, which comprises reacting one or more orthophosphoric acid esters of the formula IV

with phosphorus pentoxide in a molar ratio of (2.1 to 3.5) 1.0 in a first stage at a temperature of 20 to 180° C. in the course of 0.5 to 72 hours in a manner which is known per se, partly hydrolyzing or glycolyzing the P—O—P bonds selectively in the resulting polyphosphoric acid ester mixture of the formula V, in which $\bar{p}$ denotes an average chain length of 4 to 60,

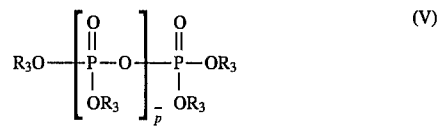

in a second stage by addition of water or a glycol of the

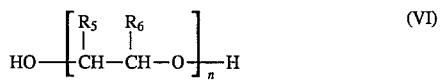

in which $R_5$, $R_6$ and n have the abovementioned meaning, at a temperature of 20° to 100° C., and reacting the resulting mixture of polyphosphoric acid partial esters of the formula VII

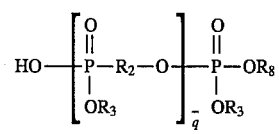

in which $R_2$ has the abovementioned meaning or is zero, $\bar{q}$ denotes a reduced average chain length of only 0.5 to 10 and $R_8$ has the meaning of $R_3$ or is an H atom, with an epoxide of the formula VIII in a third stage at a temperature of 20° to 180° C.

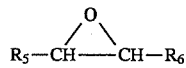

The process according to the invention furthermore optionally and preferably comprises a) carrying out the reaction during the first stage at a temperature of 60° to 120° C. in the course of 0.5 to 6 hours;

b) carrying out the partial hydrolysis of the second stage at 50° to 80° C.;

c) in the second stage, for the partial hydrolysis, adding 0.2 to 1.5 mol of water per mole of orthophosphoric acid ester of the formula (IV) employed in the first stage;

d) carrying out the reaction in the first stage in the presence of 0.1 to 2% by weight of phosphorous acid $H_3PO_3$, calculated with respect to the total amount of starting substances of the first stage;

e) carrying out the reaction during the third stage at a temperature of 70° to 140° C.

Preferred starting substances of the formula IV for the first process stage are those where $R_3$ is methyl, ethyl, butyl or butoxyethyl, methyl and ethyl being particularly suitable. Possible epoxides of the formula (VIII) are, preferably, those in which $R_5$ and $R_6$ are a hydrogen or methyl radical, in particular ethylene oxide and propylene oxide.

The composition of the mixture prepared according to the invention of virtually exclusively hydroxyl-containing components is achieved by the following procedure. In the first process stage, a molar ratio of the starting substances of (2.1 to 3.5) to 1 (products of the formula IV: $P_4O_{10}$) is chosen, polyphosphoric acid esters of the formula V having high average degrees of condensation (p=4 to 60) chiefly being obtained. By the subsequent partial hydrolysis or glycolysis of the polyphosphoric acid esters in the second stage, the average degree of condensation q is reduced to $\leq 10$, preferably to 2 to 5, by the selective cleavage of P—O—P bonds which occurs. Longer average chain lengths lead to high viscosities of the end products, which causes use problems (metering); low average chain lengths result in relatively low phosphorus contents in the end product, which leads to losses in flameproofing effectiveness. The products formed are acid esters of the formula VII which react in the third process stage to give the desired components of the formula I which carry hydroxyalkoxy groups.

The process according to the invention allows the preparation of a broad spectrum of products by variation in the nature and ratios of the amounts of the starting substances. It is therefore suitable for fulfilling specific requirements, for example in respect of average chain length, hydroxyl number, phosphorus content and viscosity.

Finally, the invention also relates to the use of the abovementioned novel mixtures of oligomeric phosphoric acid esters which carry hydroxyalkoxy groups as reactive flameproofing agents in polyurethane foams.

EXAMPLE 1

700 g (3.84 mol) of triethyl phosphate and 10.8 g of phosphorous acid were initially introduced into a reactor equipped with a stirrer, thermometer, gas inlet tube and reflux condenser. 454.5 g (1.6 mol) of $P_4O_{10}$ were added, with exclusion of atmospheric moisture and with vigorous stirring, such that the temperature did not exceed 40° C. The mixture was then heated first at 60° C. for one hour and then at 90° C. for 5 hours. 34.6 g (1.92 mol) of water were slowly added to the cooled, yellowish reaction mixture, with external cooling with ice, such that the reaction temperature reached a maximum of 70° C. After the mixture had been stirred at 70° C. for 1 hour, ethylene oxide was passed in at a temperature of 130°–140° C. until vigorous reflux was to be observed in the condenser charged with methanol and dry ice. Following an after-reaction at 130°–140° C. for 1 hour, the excess ethylene oxide which remained was removed from the reaction mixture by passing through a vigorous stream of nitrogen. 1813 g of a pale yellowish liquid having a Brookfield viscosity of 1570 mPa.s (25° C.), an acid number of 0.9 mg of KOH/g, a hydroxyl number of 125 mg of KOH/g and a phosphorus content of 17.7% were thus obtained. The mixture is composed of products of the formula I where q is 0 (approx. 5% by weight), q is 1 (approx. 10% by weight), q is 2 (approx. 15% by weight), q is 3 (approx. 40% by weight), q is 4 (approx. 15% by weight), q is 5 (approx. 10% by weight), q is 6 (approx. 5% by weight), in each case $R_3$ being ethyl (m is 0, $R_7$ is ethyl) and $R_5$ and $R_6$ being H.

EXAMPLE 2

560 g (3.08 tool) of triethyl phosphate, 9.1 g of phosphorous acid, 384 g (1.35 tool) of $P_4O_{10}$, 19.9 g (1.1 tool) of water and ethylene oxide were reacted in a reaction vessel analogous to Example 1 in accordance with the instructions given in Example 1. 1406 g of a pale yellowish liquid having a Brookfield viscosity of 3250 mPa.s (25° C.), an acid number of 0.9 mg of KOH/g, a hydroxyl number of 95 mg of KOH/g and a phosphorus content of 19.0% were obtained. The mixture is composed of products of the formula I where q is 2 (approx. 5% by weight), q is 3 (approx. 10% by weight), q is 4 (approx. 20% by weight), q is 5 (approx. 30% by weight), q is 6 (approx. 20% by weight), q is 7 (approx. 10% by weight), q is 8 (approx. 5% by weight), in each case $R_3$ being ethyl (m is 0, $R_7$ is ethyl) and $R_5$ and $R_6$ being H.

Example 3

560 g (3.08 tool) of triethyl phosphate, 3.5 g of phosphorous acid, 410 g (1.44 tool) of $P_4O_{10}$, 76.4 g (4.24 tool) of water and ethylene oxide were reacted in a reaction vessel analogous to Example 1 in accordance with the instruction given in Example 1. 2069 g of a pale yellowish liquid having a Brookfield viscosity of 500 mPa.s (25° C.), an acid number of 0.4 mg of KOH/g, a hydroxyl number of 225 mg of KOH/g and a phosphorus content of 13.3% were obtained. The mixture is composed of products of the formula I where q is 0 (approx. 25% by weight), q is 1 (approx. 40% by weight), q is 2 (approx. 20% by weight), q is 3 (approx. 10% by weight), q is 4 (approx. 5% by weight), in each case $R_3$ being ethyl (m is 0, $R_7$ is ethyl) and $R_5$ and $R_6$ being H.

EXAMPLE 4

700 g (5.0 tool) of trimethyl phosphate, 5.0 g of phosphorous acid, 591.1 g (2.08 tool) of $P_4O_{10}$ and 45.9 g (2.55 mol) of water were reacted in a reaction vessel analogously to Example 1 in accordance with the instructions given in Example 1. Ethylene oxide was then passed in at a temperature of 70°–80° C. until vigorous reflux was to be observed in the condenser charged with methanol dry ice. Following an after-reaction at 70°–80 ° C. for 1 hour, excess ethylene oxide which remained was removed from the reaction mixture by passing through a vigorous stream of nitrogen. 2280 g of a pale yellowish liquid having a Brookfield viscosity of 1920 mPa. s (25° C), an acid number of 0.5 mg of KOH/g, a hydroxyl number of 122 mg of KOH/g and a phosphorus content of 18.2% were obtained. The mixture is composed of products of the formula I where q is 0 (approx. 5% by weight), q is 1 (approx. 10% by weight) q is 2 (approx. 15% by weight), q is 3 (approx. 40% by weight), q is 4 (approx. 15% by weight), q is 5 (approx. 10% by weight), q is 6 (approx. 5% by weight), in each case $R_3$ being methyl (m is 0, $R_7$ is methyl), and $R_5$ and $R_6$ being H.

EXAMPLE 5

280 g (1.05 mol) of tributyl phosphate, 15 g of phosphorous acid, 124.4 g (0.44 mol) of $P_4O_{10}$ and 9.5 g (0.53 mol) of water were reacted in a reaction vessel analogous to Example 1 in accordance with the instructions given in Example 1. Ethylene oxide was then passed in at a temperature of 70°–80° C. until vigorous reflux was to be observed in the condenser charged with methanol and dry ice. Following an after-reaction at 100° C. for 1 hour, the excess ethylene oxide which remained was removed from the reaction mixture by passing through a vigorous stream of nitrogen. 620 g of a pale yellowish liquid having a Brookfield viscosity of 260 mPa.s (25° C.), an acid number of 0.7 mg of KOH/g, a hydroxyl number of 161 mg of KOH/g and a phosphorus content of 14.8% were obtained. The mixture is composed of products of the formula I where q is 0 (approx. 5% by weight), q is 1 (approx. 10% by weight), q is 2 (approx. 15% by weight), q is 3 (approx. 40% by weight), q is 4 (approx. 15% by weight), q is 5 (approx. 10% by weight), q is 6 (approx. 5% by weight), in each case $R_3$ being butyl (m is 0, $R_7$ is butyl) and $R_5$ and $R_6$ being H.

EXAMPLE 6

350 g (0.88 tool) of tris(butoxyethyl) phosphate, 2.5 g of phosphorous acid, 104 g (0.37 tool) of $P_4O_{10}$, 7.9 g (0.44 tool) of water and ethylene oxide were reacted in a reaction vessel analogous to Example I in accordance with the instructions given in Example 1. 598 g of a brown liquid having a Brookfield viscosity of 350 mPa.s (25° C.), an acid number of 0.2 mg of KOH/g, a hydroxyl number of 225 mg of KOH/g and a phosphorus content of 12.3% were obtained. The mixture is composed of products of the formula I where q is 0 (approx. 5% by weight), q is 1 (approx. 10% by weight), q is 2 (approx. 15% by weight), q is 3 (approx. 40% by weight), q is 4 (approx. 15% by weight), q is 5 (approx. 10% by weight), q is 6 (approx. 5% by weight), in each case $R_3$ being butoxyethyl (m is 1, $R_7$ is butyl) and $R_5$ and $R_6$ are H.

EXAMPLE 7

700 g (3.84 tool) of triethyl phosphate, 10.8 g of phosphorous acid and 454.5 g (1.6 tool) of $P_4O_{10}$ were reacted in a reaction vessel analogous to Example 1 in accordance with the instructions given in Example 1. 119.2 g (1.92 mol) of ethylene glycol were then slowly added to the cooled yellowish reaction mixture, with external cooling with ice, such that the reaction temperature reached a maximum of 70° C. After the mixture had been stirred at 70° C. for 1 hour, ethylene oxide was passed in at a temperature of 130° to 140° C. until vigorous reflux was to be observed in the condenser charged with methanol and dry ice. Following an after-reaction at 130° to 140° C. for 1 hour, the excess ethylene oxide which remained was removed from the reaction mixture by passing through a vigorous stream of nitrogen. 1801 g of a pale yellowish liquid having a Brookfield viscosity of 1420 mPa.s (25° C.), an acid number of 0.7 mg of KOH/g and a hydroxyl number of 130 mg of KOH/g were obtained. The product (formula I) where $\bar{q}$ is 3, $R_3$ is ethyl (m is 0, $R_7$ is ethyl), $R_5$ and $R_6$ are H, contained 17.6% of phosphorus (% by weight).

EXAMPLE 8

The product according to Example 1 was incorporated into a flexible polyurethane foam of the following formulation (parts by weight):

100 of polyether-polyol (®Caradol 48-2, Shell)

7.5 parts of product from Example 1

4.0 parts of water 0.4 part of dimethylethanolamine 0.2 part of tin octoate (®Desmorapid SO, Bayer)

1.0 part of silicon stabilizer (®Tegostab B 3640, Goldschmidt)

51 parts of toluylene diisocyanate (®Desmodur T 80, Bayer)

To produce the test foam, all the components—with the exception of the toluylene diisocyanate—were mixed intensively, and the latter was then added. After a starting time of 15 seconds, a rising time of 150 seconds and an after-treatment of 15 minutes in ambient air of 140° C., a flexible polyurethane foam having a density of 29 kg/m³ was obtained.

EXAMPLE 9 (COMPARISON EXAMPLE)

A test foam was produced with 7.5 parts by weight, calculated with respect to the polyol employed, of a product according to Example 1 of DE-C 20 36 595 analogously to the formulation and production instructions in Example 8. After a starting time of 22 seconds, a rising time of 134 seconds and an aftertreatment as described above, a flexible polyurethane foam having a density of 27 kg/m³ was obtained.

To determine the flame resistance of the test foams according to Example 8 (foam A) and Comparison Example 9 (foam B), the oxygen indices (LOI) were determined in accordance with ASTM-D-2863-77 and the American test FMVSS-302 (FMVSS=Federal Motor Vehicle Safety Standard) was carried out.

The foams were tested in respect of their fogging properties in accordance with DIN 75201-G.

The following results were obtained:

|  | Foam A (according to the invention) | Foam B (comparison) |
| --- | --- | --- |
| Oxygen index (ASTM-D 2863-77) FMVSS 302: | 22.5 | 23.0 |
| classification: | SE[1] | SE[1] |
| average burning zone | 22 mm | 24 mm |
| Fogging value G (DIN 75201 G) | 0.6 mg | 2.7 mg |

[1]Self-extinguishing after an average burning zone of <38 mm.

The table clearly shows the outstanding suitability of the products produced according to the invention in respect of their use as reactive flameproofing agents for polyurethane foams. While the excellent flame-retardant properties can indeed also be achieved by the known products according to DE-C 20 36 587 and 20 36 595, the superiority of the products produced by the process according to the invention is documented by the fact that this effectiveness is achieved without the use of halogen, and by the significantly reduced fogging value, which illustrates the drastically increased resistance to migration.

EXAMPLE 10 to 15

Rigid polyurethane foams having densities of 30 to 35 kg/m³ were produced in accordance with the following general formulation (parts by weight):

- 100 parts of polyether-polyol (®Caradol 585-8, Shell)
- variable parts of flameproofing agent
- 3.0 parts of water
- 2.5 parts of catalyst (dimethylcyclohexylamine)
- 2.0 parts of silicone stabilizer (®DC 193, Dow Corning GmbH)
- variable parts of blowing agent (R 141 b)
- variable parts of polyisocyanate (®Caradate 30, Shell) NCO index: 110

Burning tests in accordance with DIN 4102 Part 1 were carried out to evaluate the flame resistance. For rigid PUR foams which are to be used as building materials (insulating materials) in Germany, classification in class DIN 4102 B2 is prescribed as obligatory.

The results of the burning tests are summarized in the following table:

| Ex. | Flameproofing agent | Amount (php)[1] | DIN 4102 Flame height (mm)[2] | Class |
|---|---|---|---|---|
| 10 | Product according to Example 1 | 10 | >150 | B3 |
| 11 | Product according to Example 1 | 20 | 135–150 | B2 |
| 12 | Product according to Example 1 | 30 | <135 | B2 |
| 13 | Tris(chloroiso-propyl) phosphate | 10 | >150 | B3 |
| 14 | Tris(chloroiso-propyl) phosphate | 20 | >150 | B3 |
| 15 | Tris(chloroiso-propyl) phosphate | 30 | 135–150 | B2 |

[1] php = parts per 100 parts of polyol
[2] mean of 5 individual measurements

The tests with the product from Example 1 show its outstanding suitability as a halogen-free, reactive flameproofing agent for rigid polyurethane foams. With only 20 php, a DIN 4102 B2 classification is achieved, which is achieved when the tris (chloroisopropyl)phosphate employed on a large industrial scale is used only at a metered amount of 30 php. The use of tris(chloroisopropyl) phosphate as a flameproofing agent in rigid polyurethane foams is described in DE-AS 16 94 430.

We claim:

1. A mixture of oligomeric phosphoric acid esters which carry hydroxyalkoxy groups of the formula I

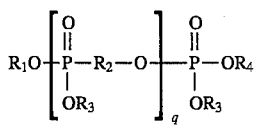

in which $R_1$ is a hydroxyl-containing radical of the formula IIa, $R_2$ is a radical of the formula III

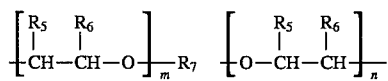

(IIa: $R_7$ = H)   (IIb: $R_7$ = $C_1$–$C_6$)   (III)

$R_3$ is a radical of the formula IIb, $R_4$ is $R_1$ or $R_3$; $R_5$, $R_6$ and $R_7$ are an H atom or an alkyl radical having 1 to 6 carbon atoms, m is to 4, n is 1 to 4 and q is 0 to 20 and $\bar{q}$ (the mean) is 0.5 to 10.

2. A mixture as in claim 1 wherein the mixture of the oligomeric phosphoric acid esters contains 0 to 35% by weight of compounds according to formula I with q=0

0 to 50% by weight of compounds according to formula I with q=1

0 to 30% by weight of compounds according to formula I with q=2

0 to 50% by weight of compounds according to formula I with q=3

0 to 50% by weight of compounds according to formula I with q=4

0 to 30% by weight of compounds according to formula I with q=5

0 to 25% by weight of compounds according to formula I with q=6

0 to 15% by weight of compounds according to formula I with q=7

0 to 15% by weight of compounds according to formula I with q=8 and in which the sum amounts to 100% by weight.

3. A mixture as in claim 1 wherein the mixture of the olibomeric phosphoric acid esters contains 2 to 15% by weight of compounds according to formula I with q=0

5 to 20% by weight of compounds according to formula I with q=1

8 to 30% by weight of compounds according to formula I with q=2

20 to 50% by weight of compounds according to formula I with q=3

8 to 30% by weight of compounds according to formula I with q=4

5 to 30% by weight of compounds according to formula I with q=5

2 to 15% by weight of compounds according to formula I with q=6 and in which the sum amounts to 100% by weight.

4. A mixture as in claim 1 wherein the mixture of the olibomeric phosphoric acid esters contains 15 to 35% by weight of compounds according to formula I with q=0

30 to 50% by weight of compounds according to formula I with q=1

10 to 30% by weight of compounds according to formula I with q=2

5 to 20% by weight of compounds according to formula I with q=3

2 to 10% by weight of compounds according to formula I with q=4 and in which the sum amounts to 100% by weight.

5. A process for the preparation of the mixture as claimed in claim 1, which comprises reacting one or more orthophosphoric acid esters of the formula IV

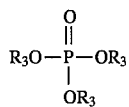  (IV)

with phosphorus pentoxide in a molar ratio of (2.1 to 3.5): 1.0 in a first stage at a temperature of 20 to 180° C. in the course of 0.5 to 72 hours partly hydrolyzing or glycolyzing the P—O—P bonds selectively in the resulting polyphosphoric acid ester mixture of the formula V,

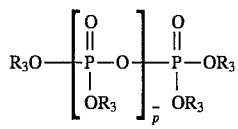  (V)

in which $\bar{p}$ denotes an average chain length of 4 to 60, in a second stage by addition of water or a glycol of the formula VI

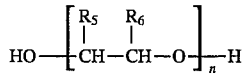  (VI)

in which $R_5$, $R_6$ and n have the abovementioned meaning, at a temperature of 20° to 100° C., and reacting the resulting mixture of polyphosphoric acid partial esters of the formula VII

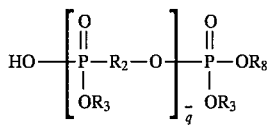  (VII)

in which $R_2$ has the abovementioned meaning or is zero, $\bar{q}$ denotes a reduced average chain length of only 0.5 to 10 and $R_8$ has the meaning of $R_3$ or is an H atom, with an epoxide of the formula VIII in a third stage at a temperature of 20° to 180° C.

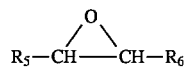  (VIII)

* * * * *